United States Patent
Yamada et al.

(10) Patent No.: US 9,822,091 B2
(45) Date of Patent: Nov. 21, 2017

(54) METHOD FOR PRODUCING ELLAGIC ACID COMPOSITION

(71) Applicant: KAO CORPORATION, Tokyo (JP)

(72) Inventors: Yasushi Yamada, Narita (JP); Tetsuya Abe, Edogawa-ku (JP); Akihiro Uda, Edogawa-ku (JP); Masanori Matsuura, Kawasaki (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/904,014

(22) PCT Filed: Jun. 13, 2014

(86) PCT No.: PCT/JP2014/065694
§ 371 (c)(1),
(2) Date: Jan. 8, 2016

(87) PCT Pub. No.: WO2015/005060
PCT Pub. Date: Jan. 15, 2015

(65) Prior Publication Data
US 2016/0159764 A1    Jun. 9, 2016

(30) Foreign Application Priority Data

Jul. 11, 2013   (JP) ................................. 2013-145088

(51) Int. Cl.
| | | |
|---|---|---|
| C07D 311/78 | (2006.01) | |
| A61K 31/366 | (2006.01) | |
| A23L 33/105 | (2016.01) | |
| A23L 2/52 | (2006.01) | |

(52) U.S. Cl.
CPC .............. *C07D 311/78* (2013.01); *A23L 2/52* (2013.01); *A23L 33/105* (2016.08); *A61K 31/366* (2013.01); *A23V 2002/00* (2013.01)

(58) Field of Classification Search
CPC .................................................. C07D 311/78
See application file for complete search history.

(56) References Cited

U.S. PATENT DOCUMENTS

| | | | |
|---|---|---|---|
| 8,021,699 B2 * | 9/2011 | Kudo et al. ............... | A23L 2/38 424/725 |
| 2007/0202205 A1 | 8/2007 | Tsujita et al. | |
| 2009/0087500 A1 | 4/2009 | Yoshikawa et al. | |

FOREIGN PATENT DOCUMENTS

| | | |
|---|---|---|
| CN | 101448411 A | 6/2009 |
| JP | 7-59539 A | 3/1995 |
| JP | 10-236970 A | 9/1998 |
| JP | 2003-208 A | 1/2003 |
| JP | 2003-81826 A | 1/2003 |
| JP | 2004-173504 A | 6/2004 |
| JP | 2005-281204 A | 10/2005 |
| JP | 2008-512345 A | 4/2008 |
| JP | 2012-17322 A | 1/2012 |
| JP | 2013-13392 A | 1/2013 |
| WO | WO 2007/135767 A1 | 11/2007 |
| WO | WO 2014/104157 A1 | 7/2014 |

OTHER PUBLICATIONS

International Search Report, issued in PCT/JP2014/065694, dated Sep. 16, 2014.

* cited by examiner

*Primary Examiner* — Noble E Jarrell
*Assistant Examiner* — John S Kenyon
(74) *Attorney, Agent, or Firm* — Birch, Stewart, Kolasch & Birch, LLP

(57) ABSTRACT

Provided is a production method for an ellagic acid composition excellent in solubility in water. The production method for an ellagic acid composition includes the steps of: mixing an aqueous medium with a raw material which contains a guava leaf extract and which contains, in solids thereof, 1 to 5% by mass of free ellagic acid to prepare a material for heat treatment; and subjecting the material for heat treatment to heat treatment at from 100 to 180° C.

16 Claims, No Drawings

METHOD FOR PRODUCING ELLAGIC ACID COMPOSITION

FIELD OF THE INVENTION

The present invention relates to a production method for an ellagic acid composition.

BACKGROUND OF THE INVENTION

Ellagic acid is a compound which is contained in plants such as strawberry, apple, guava, and tara and which has a polyphenol structure. Ellagic acid is known to have physiological functions such as a whitening effect and an antioxidant effect.

However, ellagic acid has low solubility in water and is hardly used in an aqueous product. Accordingly, a technology for solubilizing ellagic acid in water has been investigated, and for example, an α-glycoside obtained by bonding one or more molecules of a sugar to ellagic acid (Patent Document 1) has been reported. There has also been reported a method involving forming fine particles of ellagic acid by a mixing with a crystal growth inhibitor and a water-soluble polymer to disperse the particles stably (Patent Document 2).

Meanwhile, based on recent health trends, an α-amylase inhibitory action of a guava leaf extract solution has attracted attention, and for example, soft drinks each containing a guava leaf extract solution or the like have been developed (for example, Patent Documents 3 and 4).

The guava leaf extract solution contains ellagic acid, and forms precipitates at room temperature due to its poor solubility in water. Accordingly, in order to suppress deterioration of appearance of a drink, there have been proposed, for example, a method involving removing fine crystal nuclei of free ellagic acid from a guava leaf extract solution by microfiltration (Patent Document 3) and a method involving extracting guava leaves with hot water at from 90 to 98° C., concentrating the extract thus obtained to a Brix sugar content of from 20 to 30, and subjecting the resultant concentrate to freeze drying (Patent Document 4).

CITATION LIST

Patent Document

[Patent Document 1] JP-A-2005-281204
[Patent Document 2] JP-A-2003-81826
[Patent Document 3] JP-A-2003-208
[Patent Document 4] WO 2007/135767 A1

SUMMARY OF THE INVENTION

The present invention provides a production method for an ellagic acid composition, comprising the steps of: mixing an aqueous medium with a raw material which contains a guava leaf extract and which contains, in solids thereof, 1 to 5% by mass of free ellagic acid to prepare a material for heat treatment; and subjecting the material for heat treatment to heat treatment at from 100° C. to 180° C., and an ellagic acid composition obtained by the production method.

DETAILED DESCRIPTION OF THE INVENTION

An α-glycoside of ellagic acid has high solubility in water but is expensive because of cumbersome production steps. In the method of Patent Document 2, involving using a crystal growth inhibitor such as a phosphate, there may be a problem in that an application is limited due to deterioration of the taste and flavor.

Meanwhile, in the methods of Patent Documents 3 and 4, each involving treating a guava leaf extract solution, there may be a problem in that free ellagic acid having not been dissolved in a solvent for extraction is removed to cause failure of effective use of ellagic acid itself, or ellagic acid to be obtained has insufficient solubility in water.

Therefore, the present invention relates to providing a production method for an ellagic acid composition excellent in solubility in water.

The inventors of the present invention made various investigations on technologies for solubilizing ellagic acid, and found that solubility of ellagic acid in water is not improved even by subjecting only free ellagic acid to heat treatment at 100° C. or more in the presence of an aqueous medium, while the concentration of ellagic acid dissolved in water is remarkably increased by subjecting free ellagic acid to heat treatment at 100° C. or more together with a guava leaf extract. They also found that, when a composition having been subjected to the heat treatment is subjected to spray drying or freeze drying, the composition can be dried while maintaining high solubility in water, thereby obtaining an ellagic acid composition excellent in solubility in water.

According to the present invention, the concentration of free ellagic acid dissolved in water can be increased, and an ellagic acid composition excellent in solubility can be produced at a low cost.

The present invention provides a production method for an ellagic acid composition, comprising the steps of: mixing an aqueous medium with a raw material which contains a guava leaf extract and which contains, in solids thereof, 1 to 5% by mass of free ellagic acid to prepare a material for heat treatment; and subjecting the material for heat treatment to heat treatment at from 100 to 180° C.

The guava leaf extract to be used in the present invention is an extract of leaves of guava (*Psidium guajava*)

The guava leaf extract may be obtained by subjecting guava leaves as such or dried guava leaves to an extraction step, or previously-treated guava leaves as such or dried guava leaves to an extraction step. Examples of the treatment include cutting, crushing, grinding, and pulverization or the like. The guava leaf extract may be a commercially available product such as guava leaf extract powder (Matsuura Yakugyo Co., Ltd.) and Guava Phenone (manufactured by Bizen Chemical Co., Ltd.), and extracts obtained by an extraction with various, solvents in an ordinary method.

The content of free ellagic acid in the guava leaf extract is not particularly limited, and is preferably from 1 to 5% by mass (hereinafter simply referred to as "%"), more preferably from 1 to 3%.

A solvent for the extraction is not particularly limited, and examples thereof include: water; water vapor; an alcohol, such as methanol or ethanol; subcritical or supercritical carbon dioxide; an edible fat or oil, such as soybean oil, rapeseed oil, sunflower oil, palm oil, or lard; and a mixture thereof. Of those, water, an alcohol, or a mixture thereof is preferred, and water, an alcohol having 4 or less carbon atoms, or a mixture thereof is more preferred.

Any means such as solid-liquid extraction, liquid-liquid extraction, immersion, decoction, leaching, steam distillation, reflux extraction, ultrasonic extraction, microwave extraction, or stirring may be used as extraction means for obtaining the guajava leaf extract.

Conditions for the extraction are not particularly limited, and the temperature of the extraction is preferably 0° C. or more, more preferably 20° C. or more, more preferably 50° C. or more, even more preferably 60° C. or more from the viewpoint of improving extraction efficiency. In addition, the temperature of the extraction is preferably equal to or less than the boiling point of the solvent, and is preferably 100° C. or less.

The guava leaf extract thus obtained may be a crude product or a product obtained by purifying a crude product by employing known separation and purification methods in an appropriate combination. As purification means, there are given, for example, precipitation with an organic solvent, centrifugation, ultrafiltration, treatment with an adsorbent, high-performance liquid chromatograph, and column chromatograph.

In addition, as the guava leaf extract, an extract solution or a fraction as such may be used, or may be diluted with an appropriate solvent to prepare a diluted solution. Alternatively, the guava leaf extract may be prepared to a concentrated extract, dried powder, or a paste.

In the production method of the present invention, an aqueous medium is mixed with a raw material which contains a guava leaf extract and which contains, in solids thereof, 1 to 5% of free ellagic acid to prepare a material for heat treatment, and the material for heat treatment is subjected to heat treatment.

The aqueous medium to be used in the present invention may be water or an aqueous solution of water and an organic solvent. Examples of the water include tap water, distilled water, ion-exchanged water, and purified water. The organic solvent is not particularly limited as long as the solvent can be mixed homogeneously with water. The organic solvent is preferably an alcohol having 4 or less carbon atoms, more preferably propanol and ethanol, even more preferably ethanol, from the viewpoint of being applicable to foods. The concentration of the organic solvent in the aqueous solution is preferably from 0 to 60%, more preferably from 0 to 30%, more preferably from 0 to 25%, more preferably from 0 to 20%, more preferably from 0 to 10%, more preferably from 0 to 5%, even more preferably from 0 to 2%.

Mixing of the aqueous medium with the raw material may be carried out by a well-known method such as stirring.

In the production method of the present invention, the content of the guava leaf extract in the raw material is preferably 60% or more, more preferably 70% or more, more preferably 80% or more, more preferably 90% or more, more preferably 95% or more, even more preferably 97% or more in terms of solids from the viewpoint of improving the solubility of free ellagic acid, and is preferably 100% or less, more preferably 99.5% or less from the viewpoint of increasing the content of ellagic acid. In addition, the content of the guava leaf extract in the raw material is more preferably from 60 to 100%, more preferably from 70 to 100%, more preferably from 80 to 100%, more preferably from 90 to 100%, more preferably from 95 to 100%, more preferably from 97 to 100%, even more preferably from 97 to 99.5% in terms of solids.

It should be noted that the term "solids of the guava leaf extract" as used herein refers to a mass of the guava leaf extract when the extract is in a solid state, or refers to a mass of a product obtained by drying the guava leaf extract for 3 hours in an electric thermostat dryer at 105° C. to remove volatile components when the extract is in a state other than the solid state.

The content of free ellagic acid in the solids of the raw material is from 1 to 5%, is preferably 1.2% or more, more preferably 1.5% or more, more preferably 1.8% or more, more preferably 2% or more, more preferably 2.2% or more, even more preferably 2.5% or more from the viewpoint of effectively improving physiological functions, and is preferably 5% or less, more preferably 4% or less from the viewpoint of suppressing crystallization from the solution. In addition, the content of free ellagic acid in the solids is more preferably from 1.2 to 5%, more preferably from 1.5 to 5%, more preferably from 1.8 to 5%, more preferably from 2.2 to 5%, even more preferably from 2.5 to 4%.

Ellagic acid contained in plants is known to be often present as ellagitannin, i.e., in a form in which a sugar is bonded. The term "free ellagic acid" as used herein refers not to such ellagic acid in the form in which a sugar is bonded, but to ellagic acid in a free state.

The term "solids of the raw material" as used herein refers to a residue obtained by drying the raw material for 3 hours in an electric thermostat dryer at 105° C. to remove volatile components.

In order to adjust the content of free ellagic acid to fall within the range, free ellagic acid may be added to the raw material. It should be noted that free ellagic acid includes a salt or hydrate of ellagic acid. As commercially available free ellagic acid, there are given, for example, pomegranate ellagic acid (Sabinsa Japan Corporation) and ellagic acid dihydrate (Wako Pure Chemical Industries, Ltd.) or the like.

The content of the solids in the material for heat treatment obtained by mixing the raw material and the aqueous medium is generally preferably 3 g/L or more, more preferably 3.5 g/L or more, more preferably 4.0 g/L or more, and is preferably 60 g/L or less, more preferably 50 g/L or less, from the viewpoint of flowability. In addition, the content is preferably from 3 to 60 g/L, more preferably from 3.5 to 50 g/L, even more preferably from 4.0 to 50 g/L.

The guava leaf extract is preferably dispersed or dissolved in the aqueous medium so that such concentration of the solids can be achieved.

The material for heat treatment has a pH (20° C.) of preferably 4 or more, more preferably 4.7 or more, even more preferably 4.9 or more and has a pH (20° C.) of preferably 5.8 or less, more preferably 5.5 or less, more preferably 5.4 or less, even more preferably 5.3 or less from the viewpoint of improving taste and flavor and the solubility of ellagic acid. In addition, the material for heat treatment has a pH (20° C.) of preferably from 4 to 5.8, more preferably from 5 to 5.5, more preferably from 4.7 to 5.4, even more preferably from 4.7 to 5.3.

A method of subjecting the material for heat treatment to the heat treatment is not particularly limited and a known method is applicable thereto.

The temperature in the heat treatment is from 100 to 180° C., is preferably 110° C. or more, more preferably 120° C. or more from the viewpoint of improving the solubility of ellagic acid, and is preferably 170° C. or less, more preferably 160° C. or less, even more preferably 150° C. or less from the viewpoint of heat stability. In addition, the temperature is preferably from 100 to 170° C., more preferably from 110 to 170° C., more preferably from 120 to 160° C., even more preferably from 120 to 150° C. As heating means, there are given, for example, water vapor and electricity.

The pressure in the heat treatment in terms of gauge pressure is preferably from 0 to 10 MPa, more preferably from 0.1 to 8 MPa, more preferably from 0.1 to 6 MPa, more preferably from 0.2 to 6 MPa, more preferably from 0.2 to 4 MPa, more preferably from 0.25 to 2 MPa, more preferably from 0.3 to 1.5 MPa, even more preferably from 0.3 to 0.6 MPa. In addition, the pressure is preferably set to a pressure equal to or higher than a saturated vapor pressure of water. The pressurization may be carried out using a gas, and examples of the gas to be used include an inert gas, water vapor, nitrogen gas, and helium gas or the like. The pressurization may be carried out by adjusting the pressure with a back pressure valve without using the gas.

The heat treatment may be carried out by, for example, any of a batch method, a semi-batch method, a flow reaction method, and the like. Of those, a flow reaction method is preferred because the reaction time can be easily controlled.

The time for the heat treatment is preferably from 0.1 minute to 30 minutes, more preferably from 0.2 minute to 15 minutes, even more preferably from 0.5 minute to 8 minutes after the temperature of the aqueous medium reaches a predetermined temperature, from the viewpoints of improving the solubility of ellagic acid and thermal stability.

When the heat treatment is carried out by the flow reaction method, a mean residence time calculated by dividing a volume of a high-temperature and high-pressure part of the reactor by a supply rate of the aqueous medium is employed as the time for the heat treatment.

When the heat treatment is carried out by the flow reaction method, the flow rate of the aqueous medium depends on the volume of the reactor, and is, for example, preferably from 3.3 to 200 mL/min, more preferably from 6.7 to 150 mL/min, when the reactor has a volume of 100 mL.

The production method of the present invention preferably includes the step of cooling the heat-treated solution obtained by the heat treatment to 90° C. or less, preferably 50° C. or less, even more preferably 30° C. or less. In the case of producing a liquid ellagic acid composition, the temperature is preferably 0° C. or more, more preferably 10° C. or more. During the cooling, the heat-treated solution may be mixed with stirring for from 0.5 day to 5 days, preferably from 1 day to 3 days.

The cooling rate of the heat-treated solution, which is calculated from a time required to lower the heat treatment temperature to 90° C., is preferably 0.1° C./s or more, more preferably 0.2° C./s or more, more preferably 0.5° C./s or more, more preferably 1° C./s or more, more preferably 3° C./s or more, more preferably 5° C./s or more, even more preferably 7° C./s or more.

As the cooling rate becomes larger, the solubility of free ellagic acid can be improved more. Therefore, the upper limit of the cooling rate is not particularly specified, and is, for example, preferably 100° C./s or less, more preferably 50° C./s or less, from the viewpoint of, for example, restriction on production facility or the like.

The production method of the present invention preferably further includes the step of removing an undissolved residual solid portion from the heat-treated solution, from the viewpoint of improving the solubility of an ellagic acid composition to be obtained. A method of removing the solid portion is not particularly limited, and may be, for example, centrifugation, decantation, or filtration.

The ellagic acid composition of the present invention may have a form of an aqueous solution, or a form of a paste, which is obtained by adjusting the water content. In addition, the composition may have a form of a solid matter, such as a powder, a granule, or a solid, which is obtained by removing water. As means for adjusting the water content or removing water, there are given, for example, freeze drying, evaporation to dryness, and spray drying or the like.

When the heat-treated solution is subjected to freeze drying or spray drying, the resultant heat-treated solution is preferably subjected to spray drying or freeze drying within 300 minutes after completion of the heat treatment, from the viewpoint of increasing the yield of ellagic acid. Of those, spray drying is preferred because the treatment can be completed in a short time.

The phrase "within 300 minutes" after completion of the heat treatment refers to a time between the time of completion of the heat treatment, i.e., from the time when the temperature of the heat-treated solution is lowered to less than 100° C. to the time of start of spray drying or freeze drying. The time from completion of the heat treatment to start of spray drying or freeze drying is preferably 240 minutes or less, more preferably 150 minutes or less, more preferably 120 minutes or less, even more preferably 60 minutes or less, and is preferably from 0.1 minute to 150 minutes, more preferably from 0.1 minute to 60 minutes, from the viewpoint of increasing the yield of ellagic acid.

A method for the spray drying or the freeze drying is not particularly limited, and a known method is applicable thereto.

For example, the spray drying may be carried out by spraying the heat-treated solution from a nozzle to drop the solution through hot air at from 100 to 220° C., preferably from 130 to 190° C.

In addition, the freeze drying may be carried out by freezing the heat-treated solution with liquid nitrogen or in a cooling bath, a freezer, or the like, pulverizing and sieving the resultant, and sublimating water in a vacuum. The temperature for freezing the heat-treated solution is preferably from −70 to 0° C. The absolute pressure during drying is preferably from 0.1 to 1,000 Pa, more preferably from 0.5 to 100 Pa, even more preferably from 1 to 10 Pa.

The heat-treated solution may be subjected to spray drying or freeze drying after concentration. As a method of concentrating the heat-treated solution, a general method such as concentration under reduced pressure may be employed.

After the spray drying or the freeze drying, the dried product may be subjected to classification, granulation, pulverization, or the like, if necessary.

The ellagic acid composition thus obtained is suppressed from precipitating free ellagic acid even at room temperature, and is excellent in solubility in water.

The solubility of free ellagic acid in water (25° C.) in the ellagic acid composition thus obtained is preferably 0.05 g/L or more, more preferably 0.08 g/L or more, even more preferably 0.15 g/L or more.

According to the production method of the present invention, free ellagic acid can be dissolved in water at a solubilization ratio of from 30 to 100%, more preferably from 45 to 100%, more preferably from 60 to 100%, more preferably from 65 to 100%, even more preferably from 80 to 100%. It should be noted that the solubilization ratio of free ellagic acid can be calculated by an equation described in Examples below.

In addition, the production method of the present invention has less effect on taste and flavor. Therefore, the ellagic acid composition of the present invention may be used in various foods and drinks and pharmaceutical products or the like. Examples of the foods and drinks include liquid, solid, or semi-solid foods and drinks, such as drinks, bread, noodles, confectionery, e.g., a cookie, a snack, jelly, a dairy product, a frozen food, an instant food, e.g., powder coffee, a processed starch product, a processed meat product, any other processed food, a seasoning, and a nutritional supplement. In addition, examples of the pharmaceutical products include dosage forms such as a tablet (e.g., a chewable tablet), a capsule, and a powder.

Embodiments and preferred embodiments of the present invention are described below.

<1> A production method for an ellagic acid composition, comprising the steps of: mixing an aqueous medium with a raw material which contains a guava leaf extract and which contains, in solids thereof, 1 to 5% by mass of free ellagic acid to prepare a material for heat treatment; and subjecting the material for heat treatment to heat treatment at from 100 to 180° C.

<2> The production method for an ellagic acid composition according to Item <1>, wherein a content of the guava leaf extract in the raw material is preferably 60% by mass or more, more preferably 70% by mass or more, more preferably 80% by mass or more, more preferably 90% by mass or more, more preferably 95% by mass or more, even more preferably 97% by mass or more, and is preferably 100% by mass or less, more preferably 99.5% by mass or less, in terms of solids.

<3> The production method for an ellagic acid composition according to Item <1>, wherein a content of the guava leaf extract in the raw material is preferably from 60 to 100% by mass, more preferably from 70 to 100% by mass, more preferably from 80 to 100% by mass, more preferably from 90 to 100% by mass, more preferably from 95 to 100% by mass, more preferably from 97 to 100% by mass, even more preferably from 97 to 99.5% by mass, in terms of solids.

<4> The production method for an ellagic acid composition according to any one of Items <1> to <3>, wherein a content of free ellagic acid in the solids of the raw material is preferably 1.2% by mass or more, more preferably 1.5% by mass or more, more preferably 1.8% by mass or more, more preferably 2% by mass or more, more preferably 2.2% by mass or more, even more preferably 2.5% by mass or more, is preferably 5% by mass or less, more preferably 4% by mass or less, and is preferably from 1.2 to 5% by mass, more preferably from 1.5 to 5% by mass, more preferably from 1.8 to 5% by mass, more preferably from 2.2 to 5% by mass, even more preferably from 2.5 to 4% by mass.

<5> The production method for an ellagic acid composition according to any one of Items <1> to <4>, wherein a content of the solids in the material for heat treatment is preferably 3 g/L or more, more preferably 3.5 g/L or more, even more preferably 4.0 g/L or more, is preferably 60 g/L or less, more preferably 50 g/L or less, and is preferably from 3 to 60 g/L, more preferably from 3.5 to 50 g/L, even more preferably from 4.0 to 50 g/L.

<6> The production method for an ellagic acid composition according to any one of Items <1> to <5>, wherein the material for heat treatment has a pH of preferably 4 or more, more preferably 4.7 or more, even more preferably 4.9 or more, has a pH of preferably 5.8 or less, more preferably 5.5 or less, more preferably 5.4 or less, even more preferably 5.3 or less, and has a pH of preferably from 4 to 5.8, more preferably from 5 to 5.5, more preferably from 4.7 to 5.4, even more preferably from 4.7 to 5.3.

<7> The production method for an ellagic acid composition according to any one of Items <1> to <6>, wherein the aqueous medium comprises preferably water or an aqueous solution of water and an organic solvent, more preferably water or an aqueous solution of water and an alcohol having 4 or less carbon atoms, even more preferably water or an aqueous solution of water and ethanol.

<8> The production method for an ellagic acid composition according to any one of Items <1> to <7>, wherein a temperature of the heat treatment is preferably 110° C. or more, more preferably 120° C. or more, is preferably 170° C. or less, more preferably 160° C. or less, even more preferably 150° C. or less, and is preferably from 100 to 170° C., more preferably from 110 to 170° C., more preferably from 120 to 160° C., even more preferably from 120 to 150° C.

<9> The production method for an ellagic acid composition according to any one of Items <1> to <8>, wherein a pressure in the heat treatment in terms of gauge pressure is preferably from 0 to 10 MPa, more preferably from 0.1 to 8 MPa, more preferably from 0.1 to 6 MPa, more preferably from 0.2 to 6 MPa, more preferably from 0.2 to 4 MPa, more preferably from 0.25 to 2 MPa, more preferably from 0.3 to 1.5 MPa, even more preferably from 0.3 to 0.6 MPa.

<10> The production method for an ellagic acid composition according to any one of Items <1> to <9>, wherein a time for the heat treatment is preferably from 0.1 minute to 30 minutes, more preferably from 0.2 minute to 15 minutes, even more preferably from 0.5 minute to 8 minutes after the temperature of the aqueous medium reaches a predetermined temperature.

<11> The production method for an ellagic acid composition according to any one of Items <1> to <10>, further comprising the steps of: cooling a heat-treated solution obtained by the heat treatment; and removing a solid portion from the cooled heat-treated solution.

<12> The production method for an ellagic acid composition according to any one of Items <1> to <11>, wherein a rate of cooling from a heat treatment temperature to 90° C. in the step of cooling a heat-treated solution is preferably 0.1° C./s or more, more preferably 0.2° C./s or more, more preferably 0.5° C./s or more, more preferably 1° C./s or more, more preferably 3° C./s or more, more preferably 5° C./s or more, even more preferably 7° C./s or more, and is preferably 100° C./s or less, more preferably 50° C./s or less.

<13> The production method for an ellagic acid composition according to any one of Items <1> to <12>, further comprising the step of subjecting a heat-treated solution obtained by the heat treatment to spray drying or freeze drying within 300 minutes after completion of the heat treatment.

<14> The production method for an ellagic acid composition according to Item <13>, wherein a time from completion of the heat treatment to start of the spray drying or the freeze drying is preferably 240 minutes or less, more preferably 150 minutes or less, more preferably 120 minutes or less, even more preferably 60 minutes, and is preferably from 0.1 minute to 150 minutes, more preferably from 0.1 minute to 60 minutes.

<15> The production method for an ellagic acid composition according to Item <13> or <14>, wherein the spray drying or the freeze drying is performed after concentrating the heat-treated solution obtained by the heat treatment.

<16> An ellagic acid composition, obtained by the production method of any one of Items <1> to <15>.

<17> A food and drink, comprising the ellagic acid composition of Item <16>.

EXAMPLES (Quantification of Free Ellagic Acid)

Free ellagic acid was quantified by a gradient method using a high-performance liquid chromatograph manufactured by Hitachi, Ltd. with a column Cadenza CD-C18 (4.6 mmϕ×150 mm, 3 μm) manufactured by Imtakt Corporation at a column temperature of 40° C. A 0.05 mol/L aqueous solution of acetic acid was used as a mobile phase solution A, and acetonitrile was used as a mobile phase solution B, respectively, and they were delivered at 1.0 mL/min. Gradient conditions are shown below.

| Time (min) | Solution A (%) | Solution B (%) |
|---|---|---|
| 0 | 99 | 1 |
| 10 | 90 | 10 |
| 20 | 85 | 15 |
| 40 | 10 | 90 |
| 50 | 10 | 90 |
| 50.1 | 85 | 15 |
| 60 | 85 | 15 |

The sample injection volume was 10 μL, and quantification was carried out based on an absorbance at a wavelength of 254 nm.

(pH Measurement Method)

The pH was measured using a pH meter (DKK-TOA Corporation, HM-30G) after the temperature of a sample was adjusted to 20° C.

(Measurement of Amount of Free Ellagic Acid)

The amount of free ellagic acid in the material for heat treatment was determined by dissolving the material for heat treatment in dimethylsulfoxide, filtering the solution at 25° C. with a hydrophilic polytetrafluoroethylene filter having a pore size of 0.2 ∞m, and measuring the concentration of ellagic acid dissolved.

(Evaluation of Solubility)

The solubility of free ellagic acid in water in an ellagic acid composition after drying was determined by: adding the ellagic acid composition to distilled water so that the amount of solids was one in an aqueous solution or a suspension before drying; shaking the mixture at 25° C. for 5 minutes; filtering the resultant with a cellulose acetate membrane filter having a pore size of 0.2 μm; and measuring the concentration of ellagic acid dissolved therein.

(Calculation of Solubilization Ratio)

Solubilization ratio (%) of free ellagic acid=[(Mass of free ellagic acid dissolved in water or aqueous medium)/(Mass of free ellagic acid in material for heat treatment)]×100

Example 1

5.0 g of guava leaf extract powder (manufactured by Matsuura Yakugyo Co., Ltd., free ellagic acid content: 2%) was added to 1,250 mL of distilled water to prepare a material for heat treatment, and the material for heat treatment was stirred homogeneously in a slurry supply tank. The material for heat treatment had a pH of 5.1. The concentration of solids and concentration of free ellagic acid in the material for heat treatment, and the concentration of free ellagic acid in solids of the raw material are as shown in Table 1.

The solution in the slurry supply tank was fed to a stainless-steel flow reactor having an inner volume of 100 mL (manufactured by Nitto Koatsu Co., Ltd.) at 100 mL/min, and was subjected to heat treatment at 110° C. (mean residence time: 1 minute). The pressure was adjusted to 0.3 MPa (gauge pressure) with an outlet valve. The heat-treated solution was discharged from the outlet of the reactor and cooled to room temperature (25° C.) with a heat exchanger, and the pressure was returned to atmospheric pressure via the outlet valve, followed by recovery. The cooling rate determined from the time of cooling from 110° C. to 90° C. was 7.88° C./s. A part of the heat-treated solution was sampled, and the amount of free ellagic acid dissolved in the aqueous medium was measured to determine a solubilization ratio. In addition, the pH of the heat-treated solution was measured.

Subsequently, the heat-treated solution was subjected to preliminary freezing in a cooling bath at −50° C., and 30 minutes after completion of the heat treatment, drying under reduced pressure using a freeze dryer (manufactured by CHRIST, ALPHA1-4LSC) was started. The drying was carried out at an absolute pressure of 1 Pa. 72 hours later, an ellagic acid composition was obtained in a powder form. The amount of free ellagic acid dissolved in water was measured using the ellagic acid composition powder to determine a solubilization ratio.

Example 2

The same processes were performed as in Example 1 except that the heat treatment temperature was changed to 120° C.

Example 3

The same processes were performed as in Example 1 except that the heat treatment temperature was changed to 150° C. and the gauge pressure was changed to 0.6 MPa.

Comparative Example 1

The same processes were performed as in Example 2 except that 0.11 g of ellagic acid dihydrate (manufactured by Wako Pure Chemical Industries, Ltd., free ellagic acid content: 89%) was used instead of the guava leaf extract powder. The material for heat treatment had a pH of 5.8. In addition, the concentration of solids and concentration of free ellagic acid in the material for heat treatment, and the concentration of free ellagic acid in solids of the raw material are as shown in Table 1.

Comparative Example 2

The same processes were performed as in Example 1 except that the heat treatment temperature was changed to 80° C.

Example 4

The same processes were performed as in Example 2 except that the amount of the guava leaf extract powder was changed to 10 g. Thus, a heat-treated solution was collected. The material for heat treatment had a pH of 5.0. In addition, the concentration of solids and concentration of free ellagic acid in the material for heat treatment, and the concentration of free ellagic acid in solids of the raw material are as shown in Table 1.

15 minutes after completion of the heat treatment, the heat-treated solution was fed to a spray dryer (manufactured by Yamato Scientific Co., Ltd., ADL311S, inlet air temperature: 160° C., outlet air temperature: 76° C.) at a flow rate of 6.5 g/min. Thus, an ellagic acid composition was obtained in a powder form.

Example 5

The same processes were performed as in Example 4 except that the amount of the guava leaf extract powder was changed to 25 g. The material for heat treatment had a pH of 5.0. In addition, the concentration of solids and concentration of free ellagic acid in the material for heat treatment, and the concentration of free ellagic acid in solids of the raw material are as shown in Table 1.

Example 6

The same processes were performed as in Example 4 except that the amount of the guava leaf extract powder was changed to 62.5 g. The material for heat treatment had a pH of 4.9. In addition, the concentration of solids and concentration of free ellagic acid in the material for heat treatment, and the concentration of free ellagic acid in solids of the raw material are as shown in Table 1.

Example 7

The same processes were performed as in Example 4 except that 10 g of the guava leaf extract powder and 0.20 g of ellagic acid dihydrate were used. The material for heat treatment had a pH of 5.1. In addition, the concentration of solids and concentration of free ellagic acid in the material for heat treatment, and the concentration of free ellagic acid in solids of the raw material are as shown in Table 1.

Comparative Example 3

The same processes were performed as in Example 4 except that 10 g of the guava leaf extract powder and 0.45 g of ellagic acid dihydrate were used. The material for heat treatment had a pH of 5.1. In addition, the concentration of solids and concentration of free ellagic acid in the material for heat treatment, and the concentration of free ellagic acid in solids of the raw material are as shown in Table 1.

Example 8

2.0 g of guava leaf extract powder (Matsuura Yakugyo Co., Ltd., free ellagic acid content: 2%) was added to 100 mL of distilled water to prepare a material for heat treatment. The material for heat treatment had a pH of 5.0. In addition, the concentration of solids and concentration of free ellagic acid in the material for heat treatment, and the concentration of free ellagic acid in solids of the raw material are as shown in Table 1.

The material for heat treatment was subjected to heat treatment in a stainless-steel batch-type reactor having an inner volume of 190 mL (manufactured by Nitto Koatsu Co., Ltd.). After the temperature reached to 120° C., the solution was maintained for 1 minute, and cooled to room temperature (25° C.) by immersing the reactor in a cooling bath. The cooling rate determined from the time of cooling from 120° C. to 90° C. was 0.55° C./s.

15 minutes after completion of the heat treatment, the heat-treated solution was fed to a spray dryer (manufactured by Yamato Scientific Co., Ltd., ADL311S, inlet air temperature: 160° C., outlet air temperature: 76° C.) at a flow rate of 6.5 g/min. Thus, an ellagic acid composition was obtained in a powder form.

Example 9

A heat-treated solution was obtained in the same processes as in Example 5, and 300 minutes after completion of the heat treatment, the solution was fed to the spray dryer. Thus, an ellagic acid composition was obtained in a powder form.

Example 10

A heat-treated solution was obtained in the same processes as in Example 2, and concentrated to 5-fold concentration using an evaporator, and 120 minutes after completion of the heat treatment, the solution was fed to the spray dryer, and treated in the same manner as in Example 4. Thus, an ellagic acid composition was obtained in a powder form.

Example 11

The same processes were performed as in Example 2 except that 5 g of Guava Phenone (manufactured by Bizen Chemical Co., Ltd., ellagic acid content: 1.2%) was used as the guava leaf extract powder. The material for heat treatment had a pH of 5.2. In addition, the concentration of solids and concentration of free ellagic acid in the material for heat treatment, and the concentration of free ellagic acid in solids of the raw material are as shown in Table 1.

The results of Examples 1 to 11 and Comparative Examples 1 to 3 are shown in Table 1.

TABLE 1

| | | | Example 1 | Example 2 | Example 3 | Comparative Example 1 | Comparative Example 2 |
|---|---|---|---|---|---|---|---|
| Material for heat treatment | Concentration of solids | [g/L] | 4.00 | 4.00 | 4.00 | 0.088 | 4.00 |
| | Concentration of free ellagic acid | [g/L] | 0.08 | 0.08 | 0.08 | 0.078 | 0.08 |
| | Concentration of free ellagic acid in solids of raw material | [% by mass] | 2.0 | 2.0 | 2.0 | 89.0 | 2.0 |
| | pH | [—] | 5.1 | 5.1 | 5.1 | 5.8 | 5.1 |
| Heat treatment | Heat treatment temperature | [° C.] | 110 | 120 | 150 | 120 | 80 |
| | Heat treatment time | [min] | 1 | 1 | 1 | 1 | 1 |
| | Heat treatment pressure | [MPa] | 0.3 | 0.3 | 0.6 | 0.3 | 0.3 |
| | Coiling rate | [° C./s] | 7.88 | 7.06 | 6.84 | 7.06 | — |
| Evaluation | Concentration of free ellagic acid dissolved in aqueous medium (25° C.) | [g/L] | 0.08 | 0.08 | 0.08 | 0.006 | 0.018 |
| | Solubilization ratio | [%] | 100 | 100 | 100 | 8 | 23 |
| | pH | [—] | 5.0 | 5.0 | 5.0 | 5.8 | 5.1 |
| Drying | Time from completion of heat treatment to start of drying | [min] | 30 | 30 | 30 | 30 | 30 |
| | Drying method | [—] | Freeze drying | Freeze drying | Freeze drying | Freeze drying | Freeze drying |
| Evaluation | Concentration of free ellagic acid dissolved | [g/L] | 0.08 | 0.08 | 0.08 | 0.005 | 0.016 |

TABLE 1-continued

|  |  |  | Example 4 | Example 5 | Example 6 | Example 7 | Comparative Example 3 |
|---|---|---|---|---|---|---|---|
|  |  | in water (25° C.) |  |  |  |  |  |
|  |  | Solubilization ratio [%] | 100 | 100 | 100 | 6 | 20 |
| Material for heat treatment | Concentration of solids | [g/L] | 8.00 | 20.00 | 50.00 | 8.16 | 8.36 |
|  | Concentration of free ellagic acid | [g/L] | 0.16 | 0.40 | 1.00 | 0.30 | 0.48 |
|  | Concentration of free ellagic acid in solids of raw material | [% by mass] | 2.0 | 2.0 | 2.0 | 3.7 | 5.7 |
|  | pH | [—] | 5.0 | 5.0 | 4.9 | 5.1 | 5.1 |
| Heat treatment | Heat treatment temperature | [° C.] | 120 | 120 | 120 | 120 | 120 |
|  | Heat treatment time | [min] | 1 | 1 | 1 | 1 | 1 |
|  | Heat treatment pressure | [MPa] | 0.3 | 0.3 | 0.3 | 0.3 | 0.3 |
|  | Coiling rate | [° C./s] | 7.06 | 7.06 | 7.06 | 7.06 | 7.06 |
| Evaluation | Concentration of free ellagic acid dissolved in aqueous medium (25° C.) | [g/L] | 0.16 | 0.4 | 0.71 | 0.28 | 0.03 |
|  | Solubilization ratio | [%] | 100 | 100 | 71 | 93 | 6 |
|  | pH | [—] | 5.0 | 4.9 | 4.8 | 5.0 | 5.1 |
| Drying | Time from completion of heat treatment to start of drying | [min] | 15 | 15 | 15 | 15 | 15 |
|  | Drying method | [—] | Spray drying | Spray drying | Spray drying | Spray drying | Spray drying |
| Evaluation | Concentration of free ellagic acid dissolved in water (25° C.) | [g/L] | 0.16 | 0.40 | 0.66 | 0.28 | 0.03 |
|  | Solubilization ratio | [%] | 100 | 100 | 66 | 93 | 6 |

|  |  |  | Example 8 | Example 9 | Example 10 | Example 11 |
|---|---|---|---|---|---|---|
| Material for heat treatment | Concentration of solids | [g/L] | 20.00 | 20.00 | 4.00 | 4.00 |
|  | Concentration of free ellagic acid | [g/L] | 0.40 | 0.40 | 0.08 | 0.05 |
|  | Concentration of free ellagic acid in solids of raw material | [% by mass] | 2.0 | 2.0 | 2.0 | 1.2 |
|  | pH | [—] | 5.0 | 5.0 | 5.0 | 5.2 |
| Heat treatment | Heat treatment temperature | [° C.] | 120 | 120 | 120 | 120 |
|  | Heat treatment time | [min] | 1 | 1 | 1 | 1 |
|  | Heat treatment pressure | [MPa] | 0.3 | 0.3 | 0.3 | 0.3 |
|  | Coiling rate | [° C./s] | 0.55 | 7.06 | 7.06 | 7.06 |
| Evaluation | Concentration of free ellagic acid dissolved in aqueous medium (25° C.) | [g/L] | 0.27 | 0.4 | 0.08 | 0.05 |
|  | Solubilization ratio | [%] | 68 | 100 | 100 | 100 |
|  | pH | [—] | 5.0 | 4.9 | 4.9 | 5.1 |
| Drying | Time from completion of heat treatment to start of drying | [min] | 15 | 300 | 120 | 30 |
|  | Drying method | [—] | Spray drying | Spray drying | Spray drying | Freeze drying |
| Evaluation | Concentration of free ellagic acid dissolved in water (25° C.) | [g/L] | 0.26 | 0.18 | 0.39 | 0.05 |
|  | Solubilization ratio | [%] | 65 | 45 | 98 | 100 |

As is apparent from Table 1, ellagic acid compositions having improved solubility in water were able to be obtained by the method of the present invention.

Example 12

The same processes were performed as in Example 1 except that the heat treatment temperature was changed to 100° C.

Comparative Example 4

The same processes were performed as in Example 2 except that 0.11 g of ellagic acid dihydrate (manufactured by Wako Pure Chemical Industries, Ltd., free ellagic acid content: 89%) and 4.0 g of monoglucosyl hesperidin (Hayashibara Hesperidin S (trade name), Hayashibara Biochemical Laboratories, Inc.) were used instead of the guava leaf extract powder. The material for heat treatment had a pH of 5.5. In addition, the concentration of solids and concentration of free ellagic acid in the material for heat treatment and the concentration of free ellagic acid in solids of the raw material are as shown in Table 2.

The results of Example 12 and Comparative Example 4 are shown in Table 2.

TABLE 2

|  |  |  | Example 12 | Comparative Example 4 |
|---|---|---|---|---|
| Material for heat treatment | Kind of raw material |  | Guava leaf extract powder | Ellagic acid dihydrate and monoglucosyl hesperidin |
|  | Concentration of solids | [g/L] | 4.00 | 3.29 |
|  | Concentration of free ellagic acid | [g/L] | 0.08 | 0.078 |
|  | Concentration of free ellagic acid in solids of raw material | [% by mass] | 2.0 | 2.4 |
|  | pH | [—] | 5.1 | 5.5 |
| Heat treatment | Heat treatment temperature | [° C.] | 100 | 120 |
|  | Heat treatment time | [min] | 1 | 1 |
|  | Heat treatment pressure | [MPa] | 0.3 | 0.3 |
|  | Coiling rate | [° C./s] | 8.00 | 7.06 |
| Evaluation | Concentration of free ellagic acid dissolved in aqueous medium (25° C.) | [g/L] | 0.04 | 0.008 |
|  | Solubilization ratio | [%] | 50 | 10 |
|  | pH | [—] | 5.0 | 5.4 |
| Drying | Time from completion of heat treatment to start of drying | [min] | 30 | 30 |
|  | Drying method |  | Freeze drying | Freeze drying |
| Evaluation | Concentration of free ellagic acid dissolved in water (25° C.) | [g/L] | 0.052 | 0.009 |
|  | Solubilization ratio | [%] | 65 | 11 |

As is apparent from Table 2, when the material for heat treatment was subjected to heat treatment at 100° C., an ellagic acid composition having improved solubility in water was able to be obtained. On the other hand, even when free ellagic acid and monoglucosyl hesperidin were subjected to heat treatment at 120° C., solubility of ellagic acid in water was not improved.

Example 13

800 g of 50% hydrous ethanol heated to 65° C. was added to 40 g of guava tea leaves (manufactured by Okinawa Ukon-do Co., Ltd.), and extraction was carried out with stirring for 5 minutes. After that, the resultant was cooled with ice, roughly filtered with a metal mesh, and filtered under reduced pressure with filter paper No. 5C, thereby obtaining an extract solution. The extract solution was concentrated using an evaporator, and the concentrate was subjected to freeze drying to obtain a guava leaf extract containing 7.8 g of solids. The content of free ellagic acid in the resultant guava leaf extract was 1.5%.

The same processes were performed as in Example 2 except that the guava leaf extract thus obtained was used as the guava leaf extract powder. The material for heat treatment had a pH of 5.4. In addition, the concentration of free ellagic acid in the material for heat treatment is shown in Table 3.

Comparative Example 5

The guava leaf extract (ellagic acid content: 1.5%) obtained in Example 13 was dispersed in distilled water, and the dispersion was filtered with a 0.2-μm cellulose acetate membrane disc filter, followed by measurement of the concentration of dissolved ellagic acid by the HPLC.

The results of Example 13 and Comparative Example 5 are shown in Table 3.

TABLE 3

|  |  |  | Example 13 | Comparative Example 5 |
|---|---|---|---|---|
| Material for heat treatment | Concentration of solids | [g/L] | 4.00 | 4.00 |
|  | Concentration of free ellagic acid | [g/L] | 0.06 | 0.06 |
|  | Concentration of free ellagic acid in solids of raw material | [% by mass] | 1.5 | 1.5 |
|  | pH | [—] | 5.4 | 5.4 |
| Heat treatment | Heat treatment temperature | [° C.] | 120 | — |
|  | Heat treatment time | [min] | 1 | — |
|  | Heat treatment pressure | [MPa] | 0.3 | — |
|  | Coiling rate | [° C./s] | 7.06 | — |
| Evaluation | Concentration of free ellagic acid dissolved in aqueous medium (25° C.) | [g/L] | 0.055 | 0.014 |
|  | Solubilization ratio | [%] | 92 | 23 |
|  | pH | [—] | 5.4 | 5.4 |
| Drying | Time from completion of heat treatment to start of drying | [min] | 30 | — |
|  | Drying method |  | Freeze drying | — |
| Evaluation | Concentration of free ellagic acid dissolved in water (25° C.) | [g/L] | 0.052 | — |
|  | Solubilization ratio | [%] | 87 | — |

As is apparent from Table 3, an ellagic acid composition having improved solubility in water was able to be obtained by the method of the present invention.

The invention claimed is:

1. A production method for an ellagic acid composition, comprising the steps of:
    mixing an aqueous medium with a raw material which contains a guava leaf extract and which contains, in solids thereof, 1 to 5% by mass of free ellagic acid to prepare a material for heat treatment;
    subjecting the material for heat treatment to heat treatment at from 100 to 180° C.; and
    cooling a heat-treated solution obtained by the heat treatment;
    wherein a cooling rate from a heat treatment temperature to 90° C. in the step of cooling a heat-treated solution is 1° C./s or more and 100° C./s or less.

2. The production method for an ellagic acid composition according to claim 1, wherein a content of the guava leaf extract in the raw material is 60% by mass or more in terms of solids.

3. The production method for an ellagic acid composition according to claim 1, wherein a content of the solids in the material for heat treatment is from 3 to 60 g/L.

4. The production method for an ellagic acid composition according to claim 1, further comprising the steps of: removing a solid portion from the cooled heat-treated solution.

5. The production method for an ellagic acid composition according to claim 1, further comprising the step of subjecting a heat-treated solution obtained by the heat treatment to spray drying or freeze drying within 300 minutes after completion of the heat treatment.

6. The production method for an ellagic acid composition according to claim 5, wherein the spray drying or the freeze drying is performed after concentrating the heat-treated solution obtained by the heat treatment.

7. The production method for an ellagic acid composition according to claim 1, wherein a rate of cooling the heat-treated solution, which is calculated from a time required to lower the heat treatment temperature to 90° C., is 3° C./s or more and 100° C./s or less.

8. The production method for an ellagic acid composition according to claim 1, wherein a content of the guava leaf extract in the raw material is from 60 to 100% by mass, in terms of solids.

9. The production method for an ellagic acid composition according to claim 1, wherein a time for the heat treatment is from 0.1 minute to 30 minutes after the temperature of the aqueous medium reaches a predetermined temperature.

10. The production method for an ellagic acid composition according to claim 1, wherein the heat-treated solution obtained by the heat treatment is cooled to 50° C. or less in the step of cooling a heat-treated solution.

11. The production method for an ellagic acid composition according to claim 1, wherein the material for heat treatment has a pH of from 4 to 5.8.

12. The production method for an ellagic acid composition according to claim 1, wherein an aqueous medium is water, or an aqueous solution of water and an organic solvent.

13. The production method for an ellagic acid composition according to claim 1, wherein a concentration of the organic solvent in water or the aqueous solution of water and the organic solvent is from 0 to 60%.

14. The production method for an ellagic acid composition according to claim 1, wherein a pressure in the heat treatment in terms of gauge pressure is from 0 to 10 MPa.

15. A production method for an ellagic acid composition, comprising the steps of:
mixing an aqueous medium with a raw material which contains a guava leaf extract and which contains, in solids thereof, 1 to 5% by mass of free ellagic acid to prepare a material for heat treatment;
subjecting the material for heat treatment to heat treatment at from 100 to 180° C.;
cooling a heat-treated solution obtained by the heat treatment;
removing a solid portion from the cooled heat-treated solution; and
subjecting a heat-treated solution obtained by the heat treatment to spray drying or freeze drying within 300 minutes after completion of the heat treatment;
wherein a time for the heat treatment is from 0.1 minute to 30 minutes after the temperature of the aqueous medium reaches a predetermined temperature; and
wherein in the step of cooling a heat-treated solution, the heat-treated solution obtained by the heat treatment is cooled to 50° C. or less, and a cooling rate from a heat treatment temperature to 90° C. is 0.1° C./s or more and 100° C./s or less.

16. A production method for an ellagic acid composition, comprising the steps of:
mixing an aqueous medium with a raw material which contains a guava leaf extract and which contains, in solids thereof, 1 to 5% by mass of free ellagic acid to prepare a material for heat treatment;
subjecting the material for heat treatment to heat treatment at from 100 to 180° C.;
cooling a heat-treated solution obtained by the heat treatment;
removing a solid portion from the cooled heat-treated solution; and
subjecting a heat-treated solution obtained by the heat treatment to spray drying or freeze drying within 300 minutes after completion of the heat treatment;
wherein a time for the heat treatment is from 0.1 minute to 30 minutes after the temperature of the aqueous medium reaches a predetermined temperature;
wherein in the step of cooling a heat-treated solution, the heat-treated solution obtained by the heat treatment is cooled to 50° C. or less, and a cooling rate from a heat treatment temperature to 90° C. is 0.1° C./s or more and 100° C./s or less; and
wherein the spray drying or the freeze drying is performed after concentrating the heat-treated solution obtained by the heat treatment.

* * * * *